United States Patent
Sterud et al.

(10) Patent No.: US 7,322,988 B2
(45) Date of Patent: Jan. 29, 2008

(54) METHODS OF FORMING CATHETERS WITH SOFT DISTAL TIPS

(75) Inventors: Michael W. Sterud, Prescott, WI (US); Brandon J. Worcester, Maple Grove, MN (US); George N. Omae, Burnsville, MN (US); Michael Kuhn, Maple Grove, MN (US); Henry J. Pepin, Loretto, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 770 days.

(21) Appl. No.: 10/346,979

(22) Filed: Jan. 17, 2003

(65) Prior Publication Data
US 2004/0140585 A1 Jul. 22, 2004

(51) Int. Cl.
*A61F 11/00* (2006.01)
(52) U.S. Cl. .................. 606/108; 128/898; 264/230
(58) Field of Classification Search ................ 606/159, 606/194; 604/103.1, 535; 264/230, 248; 128/898
See application file for complete search history.

(56) References Cited

U.S. PATENT DOCUMENTS

| | | | |
|---|---|---|---|
| 4,395,806 A | 8/1983 | Wonder et al. | |
| 4,459,255 A | 7/1984 | Sheridan | |
| 4,531,943 A | 7/1985 | Van Tassel et al. | |
| 4,551,292 A | 11/1985 | Fletcher et al. | |
| 4,563,181 A | 1/1986 | Wijayarathna et al. | |
| 4,596,563 A | 6/1986 | Pande | |
| 4,753,765 A | 6/1988 | Pande | |
| 4,863,442 A | 9/1989 | DeMello et al. | |
| 4,886,506 A | 12/1989 | Lovgren et al. | |
| 4,961,809 A * | 10/1990 | Martin .................... 156/294 | |
| 5,061,257 A | 10/1991 | Martinez et al. | |
| 5,078,702 A | 1/1992 | Pomeranz | |
| 5,160,559 A | 11/1992 | Scovil et al. | |
| 5,178,158 A | 1/1993 | de Toledo | |
| 5,188,593 A | 2/1993 | Martin | |
| 5,205,830 A | 4/1993 | Dassa et al. | |
| 5,221,270 A | 6/1993 | Parker | |
| 5,234,416 A | 8/1993 | Macaulay et al. | |
| 5,240,537 A | 8/1993 | Bodicky | |
| 5,254,107 A | 10/1993 | Soltesz | |
| 5,292,311 A | 3/1994 | Cope | |
| 5,318,032 A | 6/1994 | Lonsbury et al. | |
| 5,342,383 A | 8/1994 | Thomas | |
| 5,423,773 A | 6/1995 | Jimenez | |

(Continued)

OTHER PUBLICATIONS

U.S. Appl. No. 10/146,980, filed May 16, 2002, Pepin et al.

*Primary Examiner*—Michael J. Hayes
*Assistant Examiner*—Victor Nguyen
(74) *Attorney, Agent, or Firm*—Crompton, Seager & Tufte, LLC (57) ABSTRACT

A catheter can be formed from an elongate shaft and a distal tip. The catheter can be formed by flaring a proximal end of the distal tip to form a flared proximal end and positioning the distal tip such that the flared proximal end of the distal tip overlaps a distal end of the outer layer. Heat and pressure are applied to melt and flow together a portion of the outer layer proximate the distal end of the shaft and the overlapped portion of the flared proximal end of the distal tip, thereby forming a joint between the elongate shaft and the distal tip.

22 Claims, 10 Drawing Sheets

U.S. PATENT DOCUMENTS

| | | |
|---|---|---|
| 5,425,712 A | 6/1995 | Goodin |
| 5,509,910 A | 4/1996 | Lunn |
| 5,545,149 A | 8/1996 | Brin et al. |
| 5,569,218 A | 10/1996 | Berg |
| 5,569,221 A | 10/1996 | Houser et al. |
| 5,603,705 A | 2/1997 | Berg |
| 5,674,208 A | 10/1997 | Berg et al. |
| 5,680,873 A | 10/1997 | Berg et al. |
| 5,762,637 A | 6/1998 | Berg et al. |
| 5,769,830 A | 6/1998 | Parker |
| 5,792,116 A | 8/1998 | Berg et al. |
| 5,792,124 A | 8/1998 | Horrigan et al. |
| 5,811,043 A | 9/1998 | Horrigan et al. |
| 5,820,612 A | 10/1998 | Berg |
| 5,824,041 A * | 10/1998 | Lenker et al. ............... 606/195 |
| 5,827,225 A | 10/1998 | Ma Schwab |
| 5,836,925 A | 11/1998 | Soltesz |
| 5,851,464 A * | 12/1998 | Davila et al. ............... 264/103 |
| 5,873,815 A * | 2/1999 | Kerin et al. ................. 600/114 |
| 5,897,537 A | 4/1999 | Berg et al. |
| 5,911,715 A | 6/1999 | Berg et al. |
| 5,951,929 A | 9/1999 | Wilson |
| 5,961,485 A | 10/1999 | Martin |
| 5,997,487 A | 12/1999 | Kolehmainen et al. |
| 6,103,037 A | 8/2000 | Wilson |
| 6,149,996 A | 11/2000 | Helgerson et al. |
| 6,187,130 B1 | 2/2001 | Berard et al. |
| 6,245,053 B1 | 6/2001 | Benjamin |
| 6,273,880 B1 | 8/2001 | Berg et al. |
| 6,322,586 B1 | 11/2001 | Monroe et al. |
| 2001/0010247 A1 | 8/2001 | Snow |
| 2003/0009184 A1 | 1/2003 | Pepin |

* cited by examiner

METHODS OF FORMING CATHETERS WITH SOFT DISTAL TIPS

TECHNICAL FIELD

The invention relates generally to catheters and relates more specifically to catheters having soft distal tips. In particular, the invention relates to methods of forming catheters having soft distal tips.

BACKGROUND

Catheters are employed in a number of medical procedures in which the catheter is inserted into and through a blood vessel lumen. There is a desire to provide catheters having outer diameters that are as small as possible in order to accommodate smaller vessel lumens. At the same time, there is a desire to provide catheters having inner diameters that are as large as possible to provide a larger lumen for insertion of other medical devices or passing fluids therethrough.

Consequently, catheters have been formed with thinner walls. As walls become thinner and thinner, the butt joints used to join catheter segments can become less effective, due in part to reductions in surface area between the segments to be joined. Thus, a need remains for an improved method of attaching a distal tip to a catheter shaft.

SUMMARY

The present invention is directed to forming a catheter from an elongate shaft and a distal tip. The elongate shaft can have a constant outside diameter over its length. A catheter can be formed by flaring a proximal end of the distal tip to form a flared proximal end, and positioning the distal tip such that the flared proximal end of the distal tip overlaps a distal end of the outer layer of the shaft. Heat and pressure are applied to melt and flow together the distal end of the outer layer on the shaft and the overlapped portion of the flared proximal end of the distal tip, thereby forming a joint between the elongate shaft and the distal tip.

In some embodiments, the tip material and the outer layer in the distal portion of the shaft are selected to be the same material. Upon application of heat and pressure, an integral joint is formed with superior tensile strength when compared to the tensile strength of a butt joint. Further, the material reforms under pressure, resulting in a shaft distal portion that generally maintains the constant outer diameter of the original shaft.

Accordingly, an embodiment of the present invention can be found in a method of forming a catheter having a distal end and a proximal end, the catheter including an elongate shaft and a distal tip. The elongate shaft includes an inner layer and an outer layer. In preferred embodiments, the outer layer is of generally constant outside diameter and includes a proximal segment and a distal segment. The distal tip has a distal end and a proximal end and is formed of a relatively soft material.

The catheter is formed by flaring the proximal end of the distal tip to form a flared proximal end and positioning the distal tip such that the flared proximal end of the distal tip overlaps the distal end of the outer layer. Heat and pressure are applied to melt and flow together a distal portion of the outer layer and the overlapped portion of the flared proximal end of the distal tip, thereby forming a joint between the catheter shaft and the distal tip. The tip preferably overlaps a portion of the distal segment of the outer layer. The distal segment is selected to be either the same material as the tip or a material that melts and reforms along with the tip material at a selected bonding temperature.

Another embodiment of the present invention is found in a method of forming a catheter that has an elongate shaft and a distal tip. The catheter has a distal end and a proximal end. The elongate shaft includes an inner layer and an outer layer, where the inner layer extends distally beyond the distal end of the outer layer. The distal tip has a distal end and a proximal end and is formed of a soft material.

The catheter is formed by providing an outer layer segment having a distal end and a proximal end, the outer layer segment formed of the same soft material as the distal tip. The outer layer segment is secured over the distal end of the inner layer such that the proximal end of the outer layer segment abuts the distal end of the outer layer. The proximal end of the distal tip is flared to form a flared proximal end and is positioned such that the flared proximal end of the distal tip overlaps the distal end of the outer layer segment. Heat and pressure are applied to melt and flow together the outer layer segment and the overlapped portion of the flared proximal end of the distal tip, thereby forming a joint between the catheter shaft and the distal tip.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following description should be read with reference to the drawings wherein like reference numerals indicate like elements throughout the several views. The drawings, which are not necessarily to scale, depict illustrative embodiments of the claimed invention.

Figure 1:
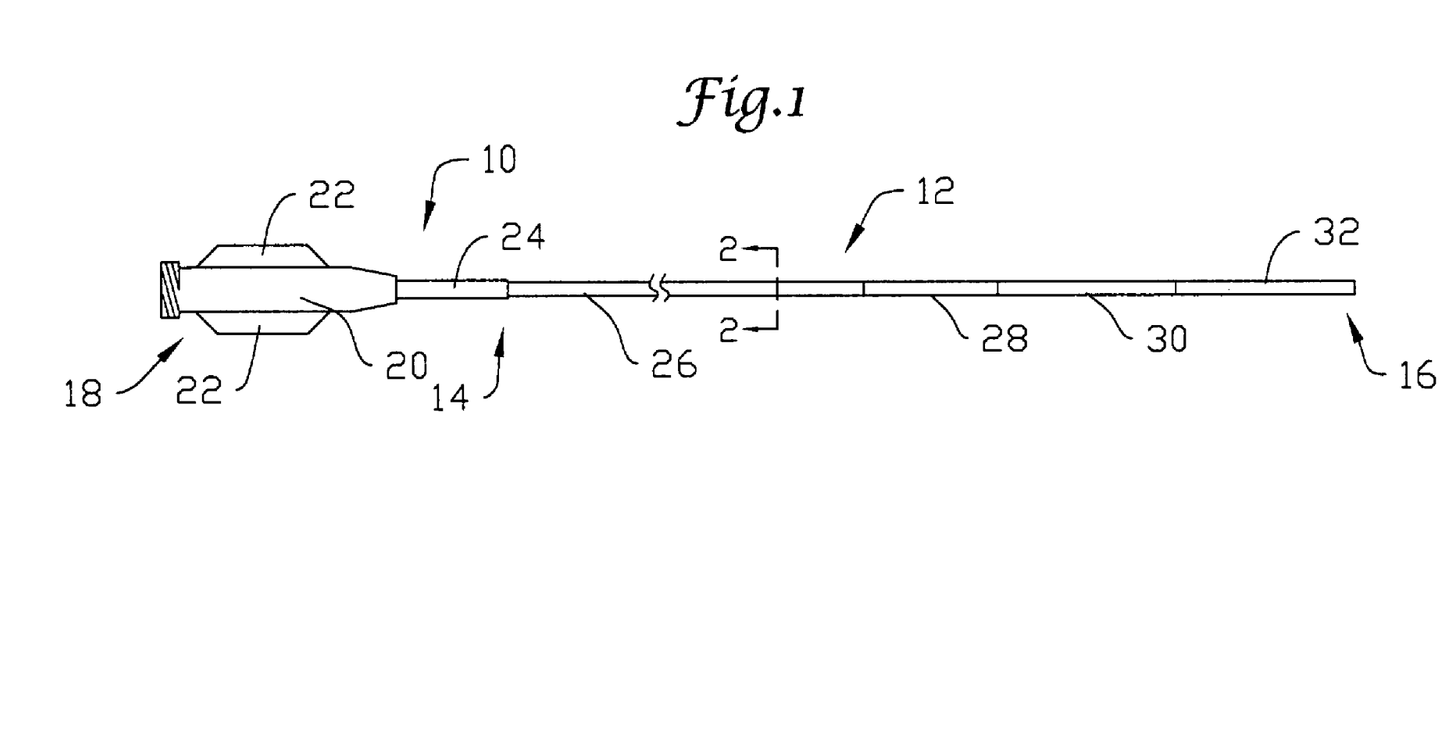
FIG. 1 is a perspective view of an intravascular catheter in accordance with an embodiment of the present invention.

FIG. 1 is a plan view of a catheter 10 in accordance with an embodiment of the present invention. The catheter 10 can be one of a variety of different catheters, but is preferably an intravascular catheter. Examples of intravascular catheters include balloon catheters, atherectomy catheters, drug delivery catheters, diagnostic catheters and guide catheters. As illustrated, FIG. 1 portrays a guide catheter, but the invention is not limited to such. Except as described herein, the intravascular catheter 10 can be manufactured using conventional techniques.

The intravascular catheter 10 can be sized in accordance with its intended use. The catheter 10 can have a length that is in the range of about 100 to 150 centimeters and can have a diameter that is in the range of about 4F (French) to 9F. In particular, the methods of making catheter 10 of the present invention can be particularly useful in manufacturing smaller diameter catheters, including catheters that are in the 4F-6F size range.

In the illustrated embodiment, the intravascular catheter 10 includes an elongate shaft 12 that has a proximal end 14 and a distal end 16. A hub and strain relief assembly 18 can be connected to the proximal end 14 of the elongate shaft 12. The hub and strain relief assembly 18 includes a main body portion 20, a pair of flanges 22 designed to improve gripping, and a strain relief 24 that is intended to reduce kinking. The hub and strain relief assembly 18 can be of conventional design and can be attached using conventional techniques.

The elongate shaft 12 can include one or more shaft segments having varying degrees of flexibility. As illustrated, the elongate shaft 12 includes a first shaft segment 26, a second shaft segment 28, and a third shaft segment 30. In some embodiments, the elongate shaft 12 can include fewer shaft segments or can include more than three segments, depending on the flexibility requirements of a particular application. The elongate shaft 12 also includes a distal tip region 32 that can include an atraumatic distal tip and will be discussed in further detail hereinafter.

Figure 2:
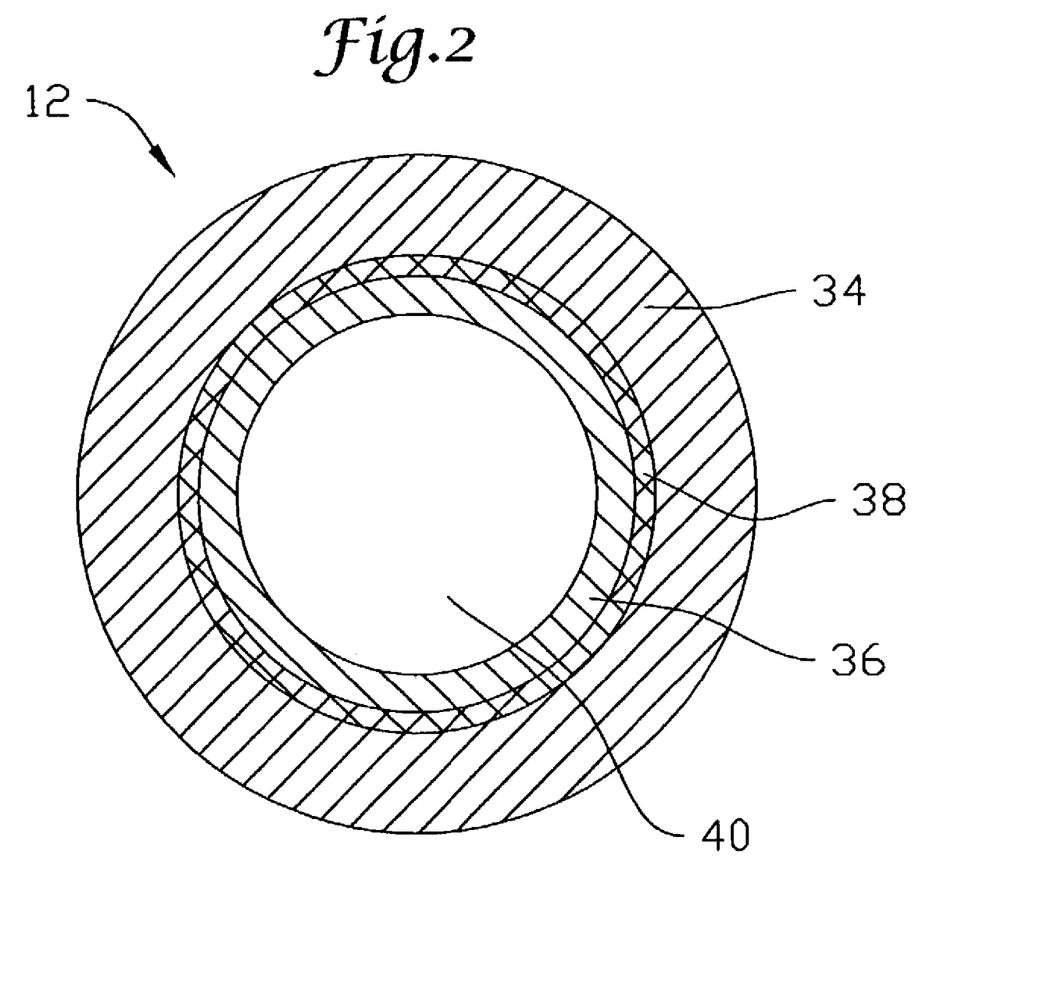
FIG. 2 is a cross-sectional view of the catheter of FIG. 1, taken along line 2-2.
Figure 4:
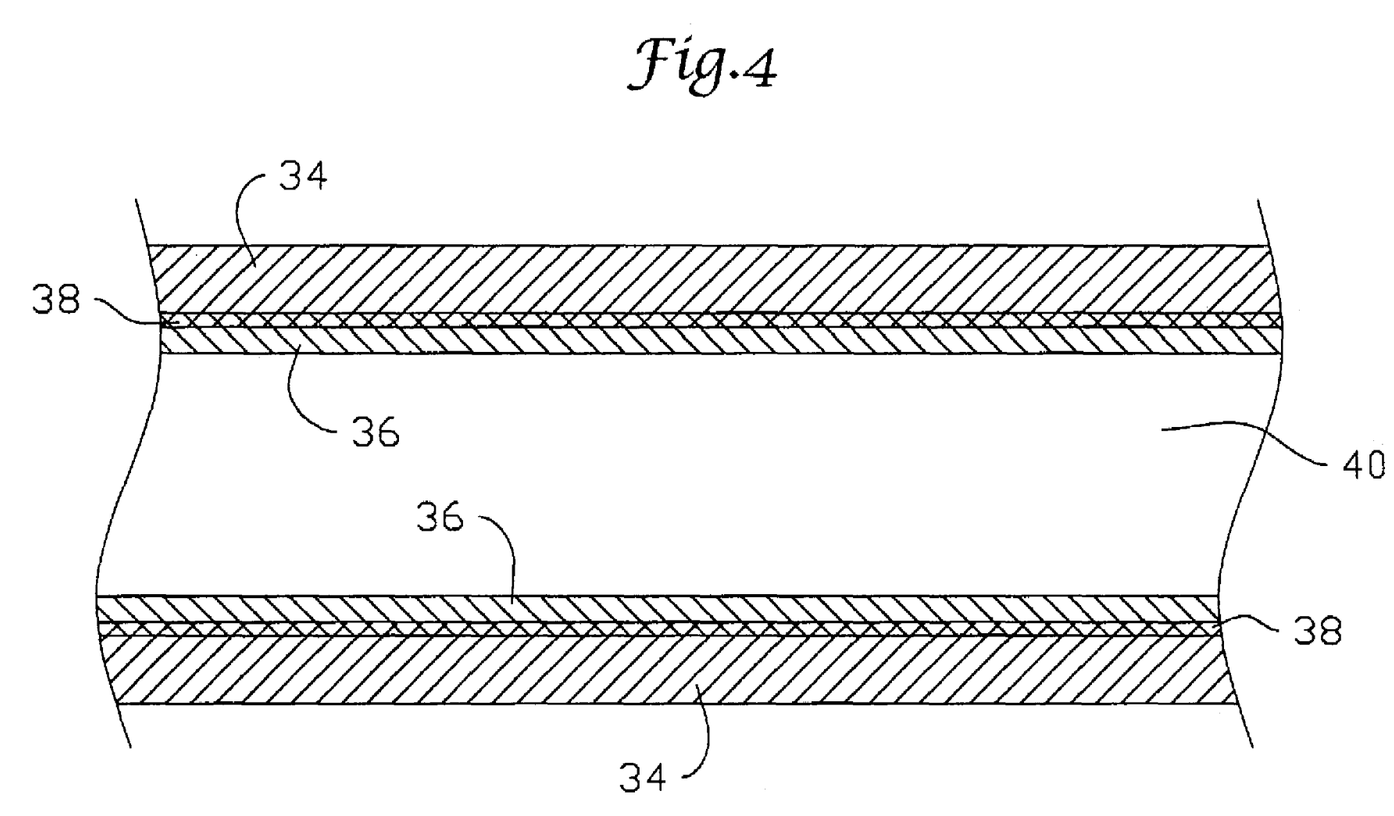
FIG. 4 is a partially sectioned view of the catheter of FIG. 1.

FIG. 2 is a cross-sectional view of the elongate shaft 12, taken along the line 2-2 of FIG. 1, while FIG. 4 is a cutaway view of the elongate shaft 12. The elongate shaft 12 includes an outer layer 34 and an inner layer 36, and can include a reinforcement layer 38 that is positioned between the inner layer 36 and the outer layer 34. The inner layer 36 defines a lumen 40 that extends through the elongate shaft 12.

Each of the shaft segments 26, 28, 30 can have a similar construction. In particular, each of the shaft segments 26, 28, 30 can include an inner layer 36 and a reinforcing layer 38 that is the same for each of the shaft segments 26, 28, 30 and an outer layer 34 that becomes more flexible in the shaft segments 26, 28, 30 closest to the distal end 16 of the catheter 10. For example, the shaft segment 26 can have an outer layer that is formed from a polymer having a hardness of 72D (Durometer), the shaft segment 28 can have an outer layer having a hardness of 68D and the shaft segment 30 can have an outer layer having a hardness of 46D.

Each of the shaft segments 26, 28, 30 can be sized in accordance with the intended function of the resulting catheter 10. For example, the shaft segment 26 can have a length of about 35 inches, the shaft segment 28 can have a length in the range of about 2 to 3 inches, and the shaft segment 30 can have a length in the range of about 1 to 1.25 inches.

The inner layer 36 is preferably a uniform material and defines a lumen 40 that can run the entire length of the elongate shaft 12 and that is in fluid communication with a lumen (not illustrated) extending through the hub assembly 18. The lumen 40 defined by the inner layer 36 can provide passage to a variety of different medical devices, and thus the inner layer 36 can include a lubricious material to reduce friction within the lumen 40. Examples of suitable materials include polytetrafluoroethylene (PTFE), better known as TEFLON®. The inner layer 36 can be dimensioned to define a lumen 40 having an appropriate inner diameter to accommodate its intended use. In some embodiments, the inner layer 36 can define a lumen 40 having a diameter of about 0.058 inches and can have a wall thickness of about 0.001 inches.

The outer layer 34 can include a thermoplastic polymer such as a co-polyester thermoplastic elastomer such as that available commercially under the ARNITEL® name. The outer layer 34 can have an inner diameter that is about equal to the outer diameter of the inner layer 36. The outer layer 34 can have an inner diameter that is slightly greater than the outer diameter of the inner layer 36 to accommodate the thickness of the reinforcing layer 38.

In some embodiments, the outer layer 34 can have an inner diameter in the range of about 0.0600 to 0.0618 inches and an outer diameter in the range of about 0.0675 to 0.0690 inches. Part or all of the outer layer 34 can include materials added to increase the radiopacity of the outer layer 34, such as 50% bismuth subcarbonate.

Figure 3:
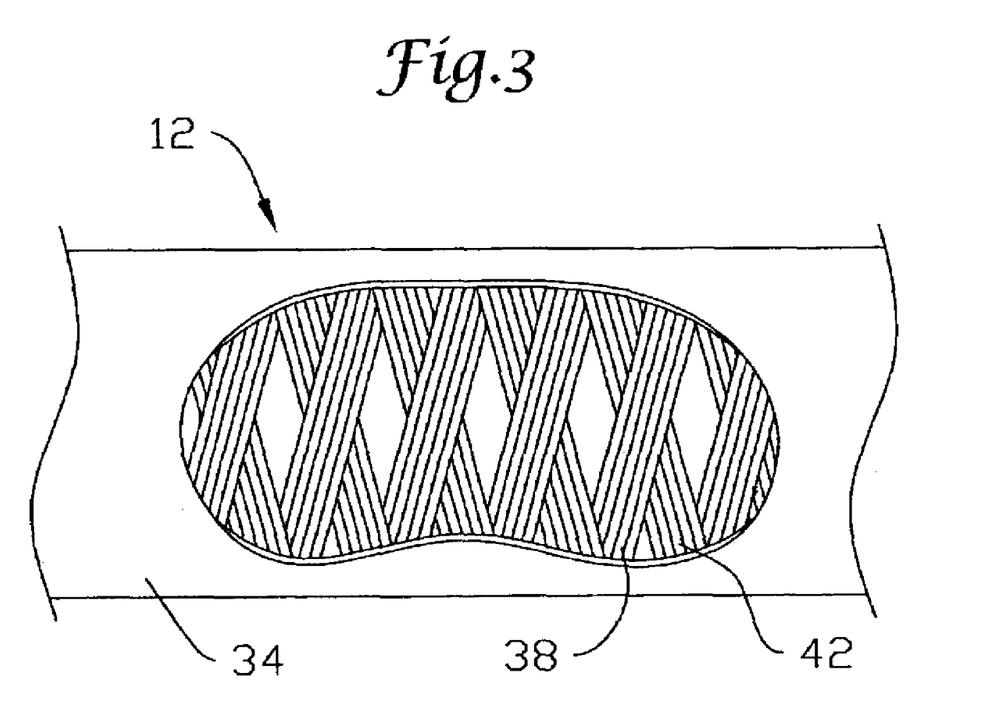
FIG. 3 is a partially sectioned fragmentary view of the catheter of FIG. 1.

A reinforcing layer 38 can be positioned between the inner layer 36 and the outer layer 34. With reference to FIG. 3, the reinforcing layer 38 can include a metal wire braid formed of stainless steel, tungsten, gold, titanium, silver, copper, platinum, or iridium. The reinforcing layer 38 can also be formed from non-metallic material such as KEVLAR® (poly paraphenylene terephthalamide) fibers, LCP (liquid crystal polymer) fibers, or glass fibers.

Whether metallic or non-metallic, the individual fibers 42 can be flat or round in cross-section and can be woven together in a variety of patterns. As illustrated, the fibers 42 are woven together in a three-over-three pattern, while other patterns such as a four-over-four or even five-over five pattern can also be used. In particular, the fibers 42 can be formed of tungsten wire having a round cross-section and a diameter of about 0.001 inches.

As noted, construction of the intravascular catheter 10 in accordance with the present invention is conventional, with the exception of how the distal tip region 32 is formed. Construction of the distal tip region 32 can be explained with reference to FIGS. 5 through 9.

Figure 5:
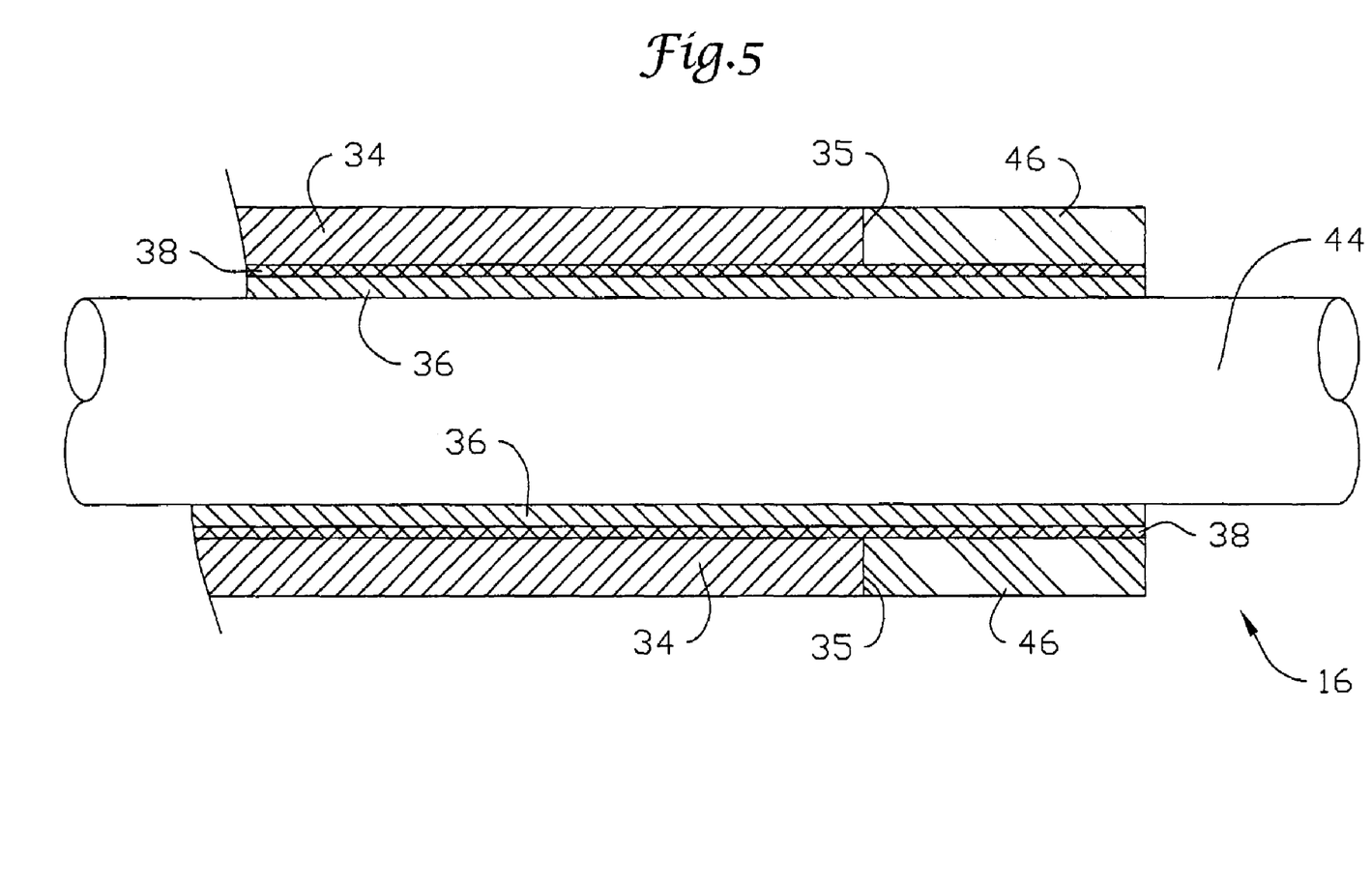
FIG. 5 is a partially sectioned view of the catheter of FIG. 1, showing the catheter positioned on a mandrel for attachment of a distal tip.

FIG. 5 is a partially sectioned view of the distal tip region 32, mounted onto a mandrel 44. The mandrel 44 is positioned within the lumen 40. The distal tip region 32 includes an inner layer 36 and a reinforcing layer 38 that both extend to the distal end 16 of the elongate shaft 12. The outer layer 34 extends to a point 35 proximal of the distal end 16 of the elongate shaft. As illustrated, the distal tip region 32 is preferably of uniform diameter and generally the same diameter as the elongate shaft 12. A distal segment 46 extends from the distal end of the outer layer 34 to the distal end 16 of the elongate shaft. The distal segment 46 can be formed of a polymer that is different from the polymer used to form the outer layer 34.

In particular, the distal segment 46 can be secured to the elongate shaft 12 by positioning the elongate shaft 12 on a mandrel 44. The distal segment 46 can be positioned over the distal end 16 of the inner layer 36, and a butt joint can be formed between the outer layer 34 and the distal segment 46.

Figure 6:
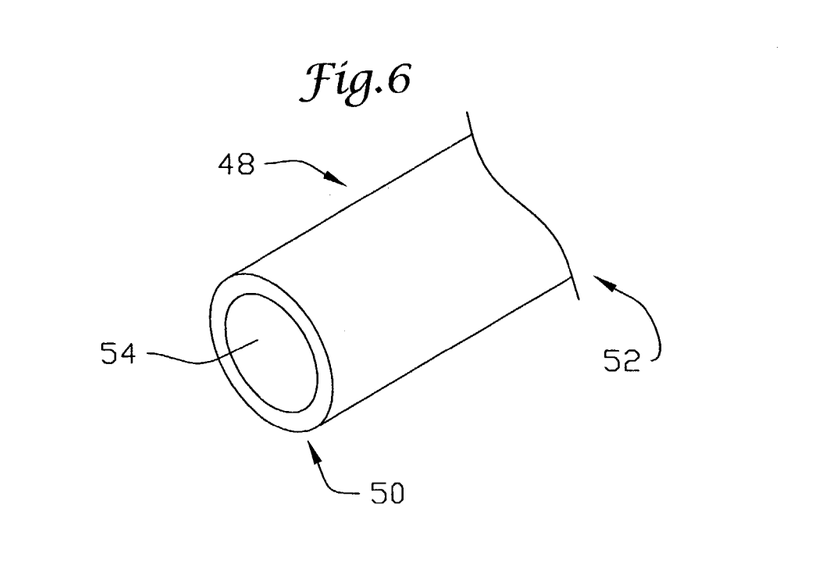
FIG. 6 is a perspective view of a distal tip in accordance with an embodiment of the present invention.

With reference to FIG. 6, a distal tip 48 has a proximal end 50 and a distal end 52. The distal tip 48 can have a generally cylindrical shape and can have a lumen 54 that extends through the distal tip 48 from its proximal end 50 to its distal end 52. In accordance with particular embodiments of the invention, the proximal end 50 of the distal tip 48 can be flared prior to attachment to the elongate shaft 12.

Figure 7:
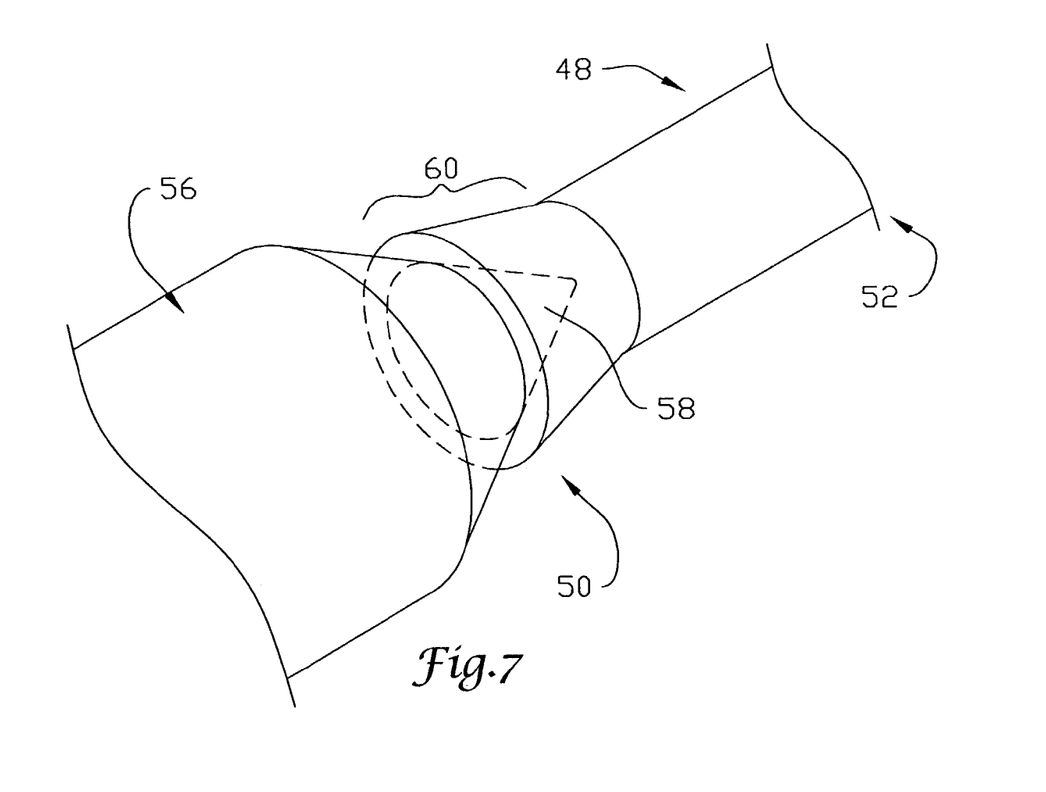
FIG. 7 is a perspective view of the distal tip of FIG. 6, illustrating a flaring technique.

FIG. 7 illustrates a technique for flaring the proximal end 50 of the distal tip 48. The flaring process can be a cold working process, although it is contemplated that the addition of heat could be beneficial. The proximal end 50 of the distal tip 48 can be processed using a flaring tool having a variety of different geometries. In some embodiments (as illustrated), a flaring tool 56 having a conical section 58 can be inserted into the proximal end 50 of the distal tip 48. By applying an axial force to the flaring tool 56, the flaring tool 56 moves distally into the lumen 54 within the distal tip 48 and expands the proximal end 50 of the distal tip 48 to form a flared end 60. The proximal end 50 of the distal tip 48 can be expanded sufficiently to permit placement of the proximal end 50 over the distal end 16 of the elongate shaft 12. In particular, the flared end 60 represents an expansion of about 16 percent over a corresponding non-flared dimension.

Figure 8:
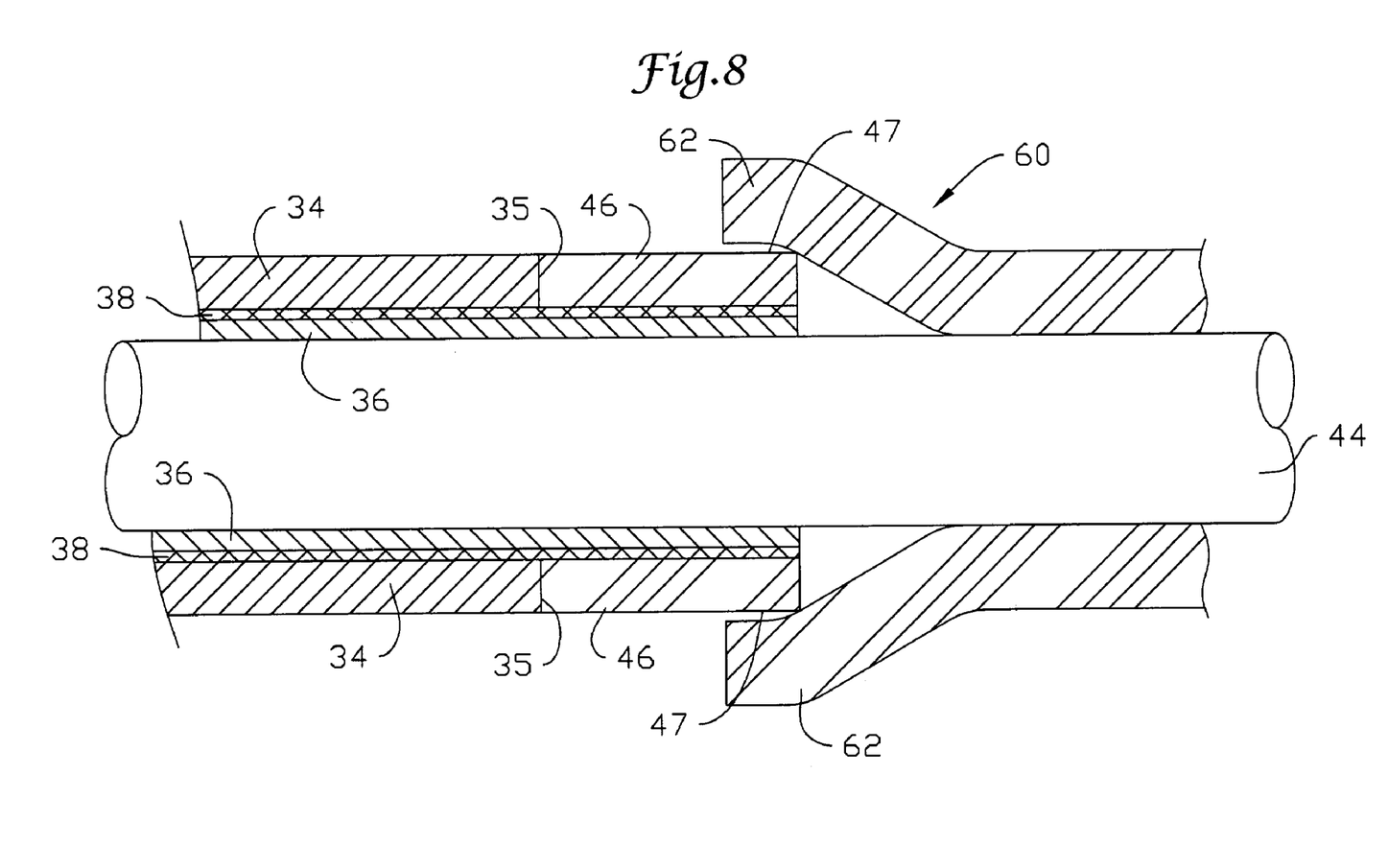
FIG. 8 is a partially sectioned view of the distal portion of the catheter of FIG. 1 and a flared distal tip positioned for attachment.

Attachment of the distal tip 48 to the distal end 16 of the elongate shaft 12 is illustrated for example in FIG. 8. The flared end 60 of the distal tip 48 is positioned over the mandrel 44 such that an overlap portion 62 of the distal tip 48 overlaps the distal portion 47 of the distal segment 46. The overlap portion 62 can overlap the distal segment 46 a distance of about 0.010 inches to about 0.030 inches. In particular, the overlap portion 62 can overlap the distal segment 46 a distance of about 0.0125 inches.

Figure 9:
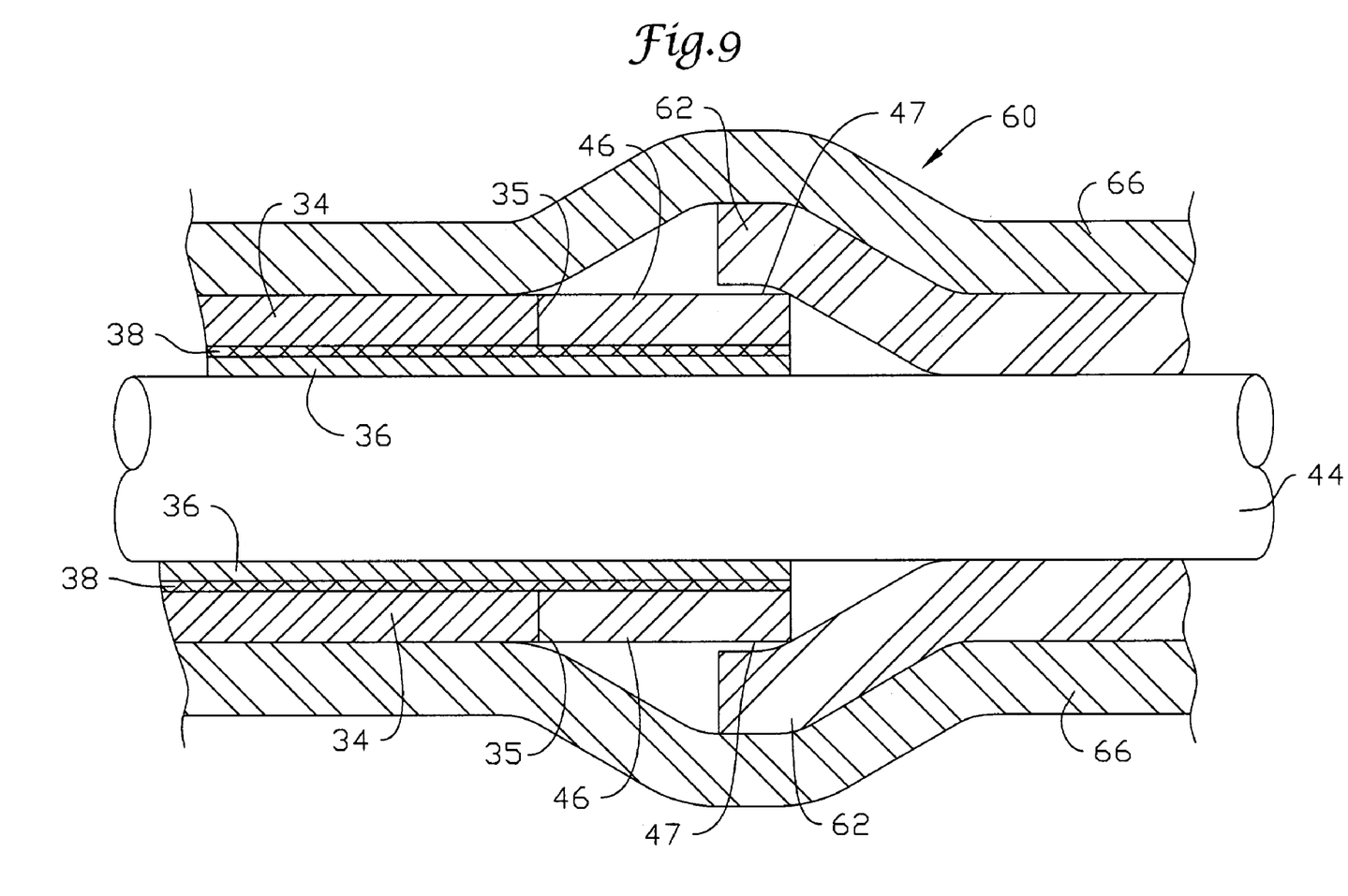
FIG. 9 is a partially sectioned view of the distal portion of the catheter of FIG. 1 and a flared distal tip positioned for attachment, showing a shrink-wrap positioned thereover.

As seen in FIGS. 8 and 9, at least part of the overlap portion 62 can conform somewhat to the distal portion 47 of the distal segment 46. In some embodiments, at least part of the overlap portion 62 can be formed with such a profile. In other embodiments, the overlap portion 62 can be formed using the illustrated flaring tool 56. After forming, at least a portion of the overlap portion 62 can relax into a position in which the distal-most portion of the overlap portion 62 returns at least partially to its pre-flared configuration.

Figure 10:
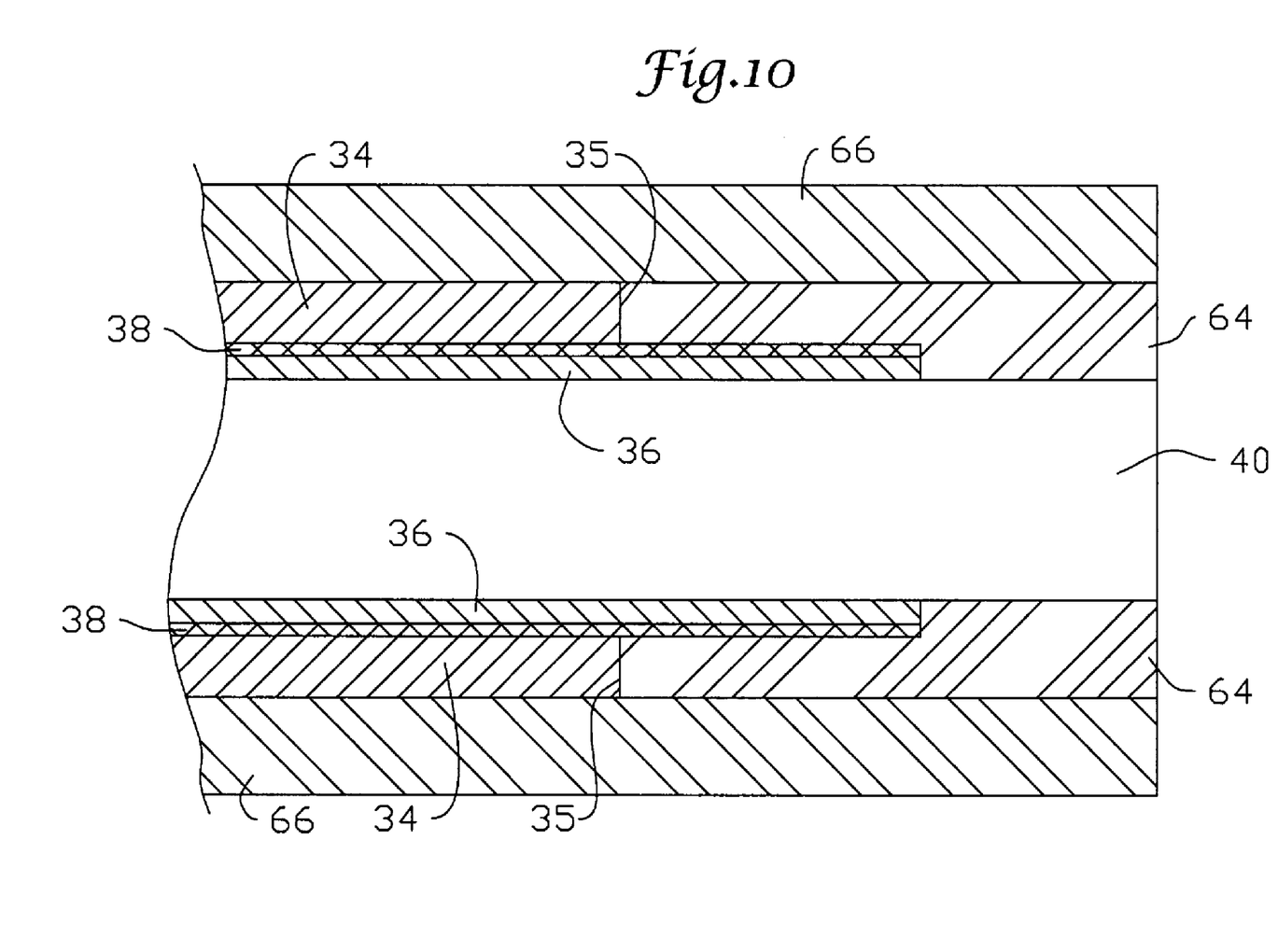
FIG. 10 is a partially sectioned view of the catheter of FIG. 1, illustrating the attached distal tip prior to removing the shrink-wrap.

As seen in FIG. 9, after the distal tip 48 has been positioned, it is secured in place by applying heat and pressure to melt and flow together the distal end 16 of the distal shaft segment 46 and the overlapped portion 62 of the flared proximal end 50 of the distal tip 48. In a particular embodiment (seen in FIG. 10), applying heat and pressure can include positioning a shrink-wrap 66 over the overlapped portion 62 and applying heat to shrink the shrink-wrap 66. As the shrink-wrap 66 is heated, it contracts and thereby applies a compressive force to the overlapped portion 62. A mechanical compressive force in addition to that applied by the shrink-wrap can also be used. After securing the distal tip 48 to the elongate shaft 12, the shrink-wrap 66 (as seen in FIG. 10) is removed.

Figure 11:
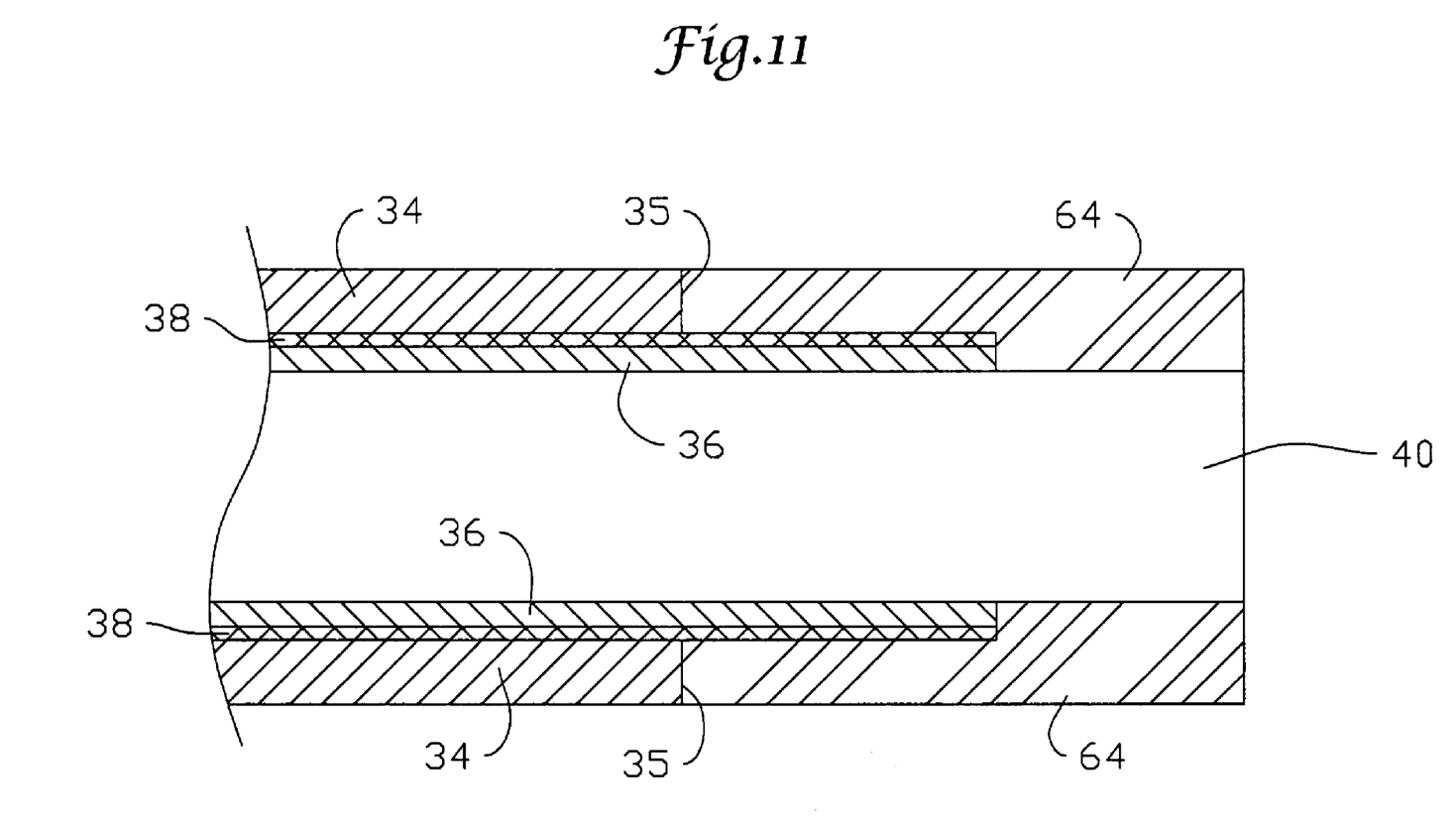
FIG. 11 is a partially sectioned view of the distal portion of the catheter of FIG. 1, illustrating the attached distal tip.

FIG. 11 shows the distal tip region 32 of the intravascular catheter 12, once the distal tip 48 has been secured. If necessary, the distal end 52 of the distal tip 48 can be trimmed to length. It can be seen that the distal segment 46 and the proximal end 50 of the distal tip 48 have melted and flowed together to form a homogenous material 64. The catheter 10 can have a diameter at the joint 35 between the outer layer 34 and the distal tip 48 that is substantially equal to the diameter of the catheter 10 at a position proximate the joint 35. In an alternative embodiment, a slight increase in diameter over the reflow region under the shrink-wrap would also be acceptable.

EXAMPLE

A guide catheter having a diameter of 5F was prepared in accordance with the present invention. For comparison purposes, a similarly sized catheter was prepared by attaching the distal tip to the elongate shaft using a butt joint. The tensile performance of each catheter was tested.

The comparison catheters had an average tensile strength of 1.54 pounds (with a standard deviation of 0.15 pounds) while the catheters made in accordance with the present invention had an average tensile strength of 1.91 pounds (with a standard deviation of 0.17 pounds). This represents an average increase in tensile strength of 24 percent.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

We claim:

1. A method of forming a catheter having an elongate shaft and a distal tip, the catheter having a distal end and a proximal end, the elongate shaft comprising an inner layer and an outer layer, the distal tip having a distal end and a proximal end, the method comprising:
    flaring a portion of the distal tip proximate the proximal end to form a flared proximal end;
    positioning the distal tip such that the flared proximal end of the distal tip overlaps the distal end of the outer layer; and
    applying heat and pressure to melt and flow together the outer layer proximate the distal end and the overlapped portion of the flared proximal end of the distal tip, thereby forming a joint between the catheter shaft and the distal tip.

2. The method of claim 1, wherein applying heat and pressure comprises positioning a shrink-wrap over the overlapped portion of the flared proximal end of the distal tip and applying heat, thereby shrinking the shrink-wrap.

3. The method of claim 2, further comprising applying a compressive force to the overlapped portion of the distal tip, in addition to that applied by the shrink wrap.

4. The method of claim 2, further comprising removing the shrink-wrap after forming the joint.

5. The method of claim 1, wherein the catheter has an outer diameter at the joint between the distal tip and the elongate shaft that is substantially equal to an outer diameter of the shaft at a position proximate the joint.

6. The method of claim 1, wherein the elongate shaft further comprises an intermediate reinforcing layer that is positioned between the inner layer and the outer layer.

7. The method of claim 6, wherein the inner layer and the intermediate reinforcing layer extend from the proximal end of the elongate shaft to the distal end of the elongate shaft.

8. The method of claim 6, wherein the outer layer comprises a proximal portion that extends from the proximal end of the elongate shaft to a position proximal of the distal end of a first polymer and a distal portion that extends from the proximal portion to the distal end of the elongate shaft, the distal portion formed of the same soft material as the distal tip.

9. The method of claim 1, wherein flaring the proximal end of the distal tip comprises increasing a diameter of the proximal end by about 16 percent.

10. The method of claim 1, wherein positioning the distal tip comprises positioning the distal tip such that about 0.010 inches to about 0.030 inches of the flared proximal end of the distal tip overlaps the distal end of the outer layer.

11. The method of claim 1, wherein positioning the distal tip comprises positioning the distal tip such that about 0.020 inches of the flared proximal end of the distal tip overlaps the distal end of the outer layer.

12. A method of forming a catheter comprising an elongate shaft and a distal tip, the catheter having a distal end and a proximal end, the elongate shaft comprising an inner layer and an outer layer, the inner layer extending distally beyond the distal end of the outer layer, the distal tip having a distal end and a proximal end, the distal tip comprising a soft material, the method comprising: providing a distal segment having a distal end and a proximal end, the distal segment formed of the same soft material as the distal tip;

securing the distal segment over the distal end of the inner layer such that the proximal end of the distal segment abuts the distal end of the outer layer;

flaring the proximal end of the distal tip to form a flared proximal end;

positioning the distal tip such that the flared proximal end of the distal tip overlaps the distal end of the distal segment; and applying heat and pressure to melt and flow together the distal segment and the overlapped portion of the flared proximal end of the distal tip, thereby forming a joint between the catheter shaft and the distal tip.

13. The method of claim 12, wherein securing the distal segment comprises:

positioning the elongate shaft over a mandrel;

positioning the distal segment over the distal end of the inner layer; and forming a butt joint between the distal end of the outer layer and the proximal end of the distal segment.

14. The method of claim 12, wherein applying heat and pressure compnses positioning a shrink-wrap over the overlapped portion of the flared proximal end of the distal tip and applying heat, thereby shrinking the shrink-wrap.

15. The method of claim 14, further comprising applying a compressive force to the overlapped portion of the distal tip, in addition to that applied by the shrink-wrap.

16. The method of claim 14, further comprising a subsequent step of removing the shrink-wrap after forming the joint.

17. The method of claim 12, wherein the catheter has an outer diameter at the joint between the distal tip and the elongate shaft that is substantially equal to an outer diameter of the shaft at a position proximate the joint.

18. The method of claim 12, wherein the soft material of the distal end of the outer layer and the soft material of the overlapping portion of the soft distal tip, as a result of melting and flowing, form a homogenous material.

19. The method of claim 12, wherein flaring the proximal end of the distal tip comprises increasing a diameter of the proximal end by about 16 percent.

20. The method of claim 12, wherein positioning the distal tip comprises positioning the distal tip such that about 0.010 inches to about 0.030 inches of the flared proximal end of the distal tip overlaps the distal end of the outer layer segment.

21. The method of claim 12, wherein positioning the distal tip comprises positioning the distal tip such that about 0.020 inches of the flared proximal end of the distal tip overlaps the distal end of the outer layer segment.

22. The method of claim 12, wherein the elongate catheter shaft has an outer diameter of less than about 0.0710 inches.

* * * * *

UNITED STATES PATENT AND TRADEMARK OFFICE
CERTIFICATE OF CORRECTION

PATENT NO. : 7,322,988 B2
APPLICATION NO. : 10/346979
DATED : January 29, 2008
INVENTOR(S) : Michael W. Sterud et al.

Page 1 of 1

It is certified that error appears in the above-identified patent and that said Letters Patent is hereby corrected as shown below:

Column 8
Line 9, delete "compnses" and insert therefor -- comprises --.

Signed and Sealed this

Twentieth Day of May, 2008

JON W. DUDAS
*Director of the United States Patent and Trademark Office*